(12) United States Patent
Anderson et al.

(10) Patent No.: US 8,258,173 B2
(45) Date of Patent: Sep. 4, 2012

(54) MELATONIN DERIVATIVES AND THEIR USE AS ANTIOXIDANTS

(75) Inventors: Rosaleen Joy Anderson, Sunderland (GB); Paul William Groundwater, Sunderland (GB); David Antony Philip Small, Aylesbury (GB); Yu Gong, Sunderland (GB)

(73) Assignee: University of Sunderland, Sunderland (GB)

( * ) Notice: Subject to any disclaimer, the term of this patent is extended or adjusted under 35 U.S.C. 154(b) by 547 days.

(21) Appl. No.: 12/515,632

(22) PCT Filed: Nov. 19, 2007

(86) PCT No.: PCT/GB2007/004416
§ 371 (c)(1),
(2), (4) Date: May 20, 2009

(87) PCT Pub. No.: WO2008/062167
PCT Pub. Date: May 29, 2008

(65) Prior Publication Data
US 2010/0063125 A1 Mar. 11, 2010

Related U.S. Application Data

(60) Provisional application No. 60/859,923, filed on Nov. 20, 2006.

(51) Int. Cl.
*A61K 31/405* (2006.01)
*A61K 31/40* (2006.01)

(52) U.S. Cl. ......................................... 514/415; 514/418

(58) Field of Classification Search ................. 514/415, 514/418
See application file for complete search history.

(56) References Cited

U.S. PATENT DOCUMENTS

| | | |
|---|---|---|
| 3,564,012 A | 2/1971 | McManus |
| 3,953,442 A | 4/1976 | Demarne |
| 4,997,845 A | 3/1991 | Flaugh |
| 5,496,957 A | 3/1996 | Glennon |

FOREIGN PATENT DOCUMENTS

| | | |
|---|---|---|
| GB | 910991 | 11/1962 |
| WO | 2005/062992 | 7/2005 |

OTHER PUBLICATIONS

Ballini, R. et al., "Conjugate addition of indoles to nitroalkenes promoted by basic alumina in solventless conditions," Adv. Synth. Catal. (2006) 348(1-2):191-196.

Faust, R. et al., "7-substituted-melatonin and 7-substituted-1-methylmelatonin analogues: effect of substituents on potency and binding affinity," Biorg. Med. Chem. (2007) 15:4543-4551.

Faust, R. et al., "Mapping the malatonin receptor. 6. Melatonin agonists and antagonists derived from 6H-isoindolo [2,1-alpha]indoles, 5,6-dihydroindolo[2,1-alpha]isoquinolines and 6,7-dihydro-5H-benzo[c]azepino[2,1-alpha]indoles," J. Med. Chem. (2000) 43:1050-1061.

Flaugh, M.E. et al., "Synthesis and evaluation of the antiovulatory activity of a variety of melatonin analogues," J Med. Chem. (1979) 22(1):63-69.

Gurkan, A.S. et al., "Synthesis of novel indole lipoic acid derivatives and their antioxidant effects on lipid peroxidation," Arch. Pharm. Chem. Life Sci. (2005) 338:67-73.

Hayashi, T. et al., "Nucleophilic substitution reaction on the nitrogen of indole nucleus: a novel synthesis of 1-aryltryptamines," Heterocycles (2002) 57(3):421-424, CAPLUS Database accession No. 2002:218429.

Mahboobi, S. et al., "Synthesis of pyrrolidin-2-ones and of staurosporine aglycon (K-252c) by intermolecular michael reaction," J. Org. Chem. (1999) 64(13):4697-4704, CAPLUS Database accession No. 1999:327324.

Mor, M. et al., "Melatonin receptor ligands: synthesis of new melatonin derivatives and comprehensive comparative molecular field analysis (CoMFA) study," J. Med. Chem. (1998) 41:3831-3844.

Spadoni, G. et al., "Conformationally restrained melatonin analogues: synthesis, binding affinity for the melatonin receptor, evaluation of the biological activity, and molecular modeling study," J. Med. Chem. (1997) 40:1990-2002.

Tsotinis, A. et al., "Mapping the melatonin receptor. 7. Subtype selective ligands based on β-substituted N-acyl-5-methoxytryptamines and β-substituted N-acyl-5-methoxy-1-methyltryptamines," J. Med. Chem. (2006) 49:3509-3519.

International Search Report and Written Opinion for Application No. PCT/GB2007/004416 dated Aug. 20, 2008 (20 pages).

*Primary Examiner* — San-Ming Hui

(74) *Attorney, Agent, or Firm* — Michael Best & Friedrich LLP

(57) ABSTRACT

The present subject matter relates generally to antioxidant compounds having the formula (I): wherein each of $R_1$, $R_2$, $R_3$, and $R_4$ are as defined below. These compounds are potentially useful as, for example, antioxidants.

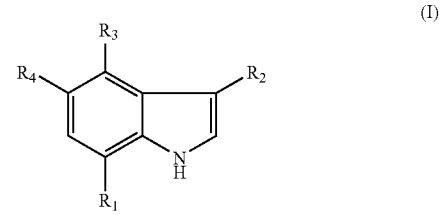

(I)

14 Claims, No Drawings

MELATONIN DERIVATIVES AND THEIR USE AS ANTIOXIDANTS

CROSS-REFERENCE TO RELATED APPLICATIONS

This patent application is a national stage filing under 35 U.S.C. 371 of International Application No. PCT/GB2007/004416, filed on Nov. 19, 2007, which claims priority benefits to U.S. Provisional Application No. 60/859,923, filed on Nov. 20, 2006. These applications are incorporated herein by reference in their entireties.

FIELD OF THE INVENTION

The present subject matter relates generally to antioxidant compounds having the formula (I):

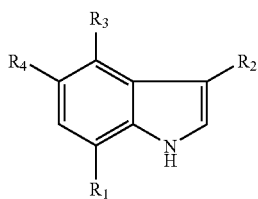

(I)

wherein each of $R_1$, $R_2$, $R_3$, and $R_4$ are as defined below. These compounds are potentially useful as, for example, antioxidants.

BACKGROUND OF THE INVENTION

The major zones of skin are the epidermal and dermal regions, with various appendages such as hair follicles, sweat glands, and sebaceous glands. The outermost layer of the skin is called the stratum corneum and is a part of the epidermis. The stratum corneum forms the barrier that keeps water in and unwanted materials out of the body. Below the stratum corneum lies the viable epidermis, which consists of 10 cell layers. The epidermis is viable tissue made up primarily (about 90-95%) of keratinocytes. Three substrata of living cells in the skin are the basal, spinous, and granular layers. These three layers provide progressive stages of differentiation and keratinization of the living keratinocytes as they move toward the skin's surface to become part of the stratum corneum.

Melanocytes synthesize the yellow, red, and brown biochromesmelanin, which are large polymers bound to proteins. Melanin is made by the melanocytes in membrane bound organelles called melanosomes. Melanocytes form a network of cells near the basal layer of stratum germinatium. Melanin absorbs light over a broad range of wavelengths (200-2400 nm), thus serving as an excellent screen against the damaging cutaneous effects of solar ultraviolet radiation. During a process termed "melanization", melanosomes are transferred from the melanocytes to the keratinocytes.

Derivatives of melatonin have antioxidant activity. Antioxidant activity may occur (a) through direct free radical scavenging and/or (b) through up-regulation of genes involved in the anti-oxidant response. Compounds which exert their antioxidant activity only through direct free radical scavenging exert an acute effect, which is limited by the half life of the compound, whereas compounds which exert their antioxidant effect through gene regulation potentially have a much longer term of effect. Mammalian cells possess signaling mechanisms that control the cells' ability to metabolize electrophiles, for example by induction of phase II enzymes such as glutathione transferase, through antioxidant/electrophile response elements (ARE) in their regulatory sequences. These antioxidant response elements are not inducible by reactive oxygen species (ROS) per se; however, a set of genes are induced in response to ROS exposure and help the cell deal with oxidative damage by controlling cell proliferation and DNA/protein repair processes, largely independent of those associated with the antioxidant response.

Reactive oxygen species (ROS) are constitutively produced in epidermal keratinocytes by specific processes, such as enzymatic oxidations and aerobic respiration. In addition, ROS can be induced by several cytokines, growth factors, and other physiological stimuli. Skin damage caused by ultraviolet (UV) radiation is also associated with ROS.

After prolonged exposure, the UV part of sunlight can cause significant damage to skin. The solar UV radiation that reaches the earth's surface is comprised of two components: UVB at a wavelength of 280-320 nm and UVA at a wavelength of 320-380 nm. UVA is weakly absorbed by most biomolecules, it is absorbed in the skin by melanin and hemoglobin, but is oxidative in nature. The oxidative nature of the UVA radiation absorbed by the melanin and hemoglobin leads to the generation reactive oxygen species. Furthermore, there is evidence from under vacuum studies that irradiation of macromolecules with UVA radiation can cause generation of hydrogen peroxide ($H_2O_2$) and that iron-catalyzed reduction of $H_2O_2$ by superoxide anion can further generate the highly reactive hydroxyl radical ($OH^-$).

Likewise, high doses of UVB also generate hydroxyl radicals ($OH^-$) and lead to DNA damage. Meanwhile, high levels of superoxide dismutase (SOD) in cells may protect the cells against UVB radiation. Superoxide dismutase (SOD), catalase (CAT), glutathione peroxidase (GSH-Px) and glutathiond reductase (GSH-Rd) are antioxidant enzymes in human cells. These enzymes are important in cellular defense against UV-induced oxidative stress. Oxidative stress of non-differentiated keratinocytes triggers the formation of a defective horny layer, the key mechanism of psoriasis.

Melatonin is a free radical scavenger. Besides $OH^-$, $O_2^-$ and $ROO^-$, melatonin neutralizes nitric oxide (NO), peroxynitrite anion and hypochlorous acid. Melatonin also activates anti-oxidative enzymes, such as superoxide dismutase (SOD), catalase (CAT), glutathione peroxidase (GSH-Px) and glutathione reductase (GSH-Rd).

By scavenging $O_2^-$, melatonin reduces the formation of $ONOO^-$ and prevents the activation of poly(ADP-ribose)synthase. Melatonin also curtails the synthesis of NO, thereby reducing the formation of $ONOO^-$. Moreover, melatonin scavenges $ONOO^-$ and $OH^-$ directly. Since the over-production of ROS contributes to acute inflammatory response, small molecules which permeate biological membranes and function as intracellular radical scavengers, such as melatonin, may be useful in the therapy of conditions associated with local or systemic inflammation.

Oxidative stress has been linked to inflammatory skin diseases, such as psoriasis, and skin diseases could result from an imbalance between pro-oxidant and antioxidant stimuli. Cytokines and growth factors can act to stimulate, specifically, the generation of superoxide anion ($O_2^-$) and hydrogen peroxide ($H_2O_2$), which act as second messengers in modulating the redox status of individual components of the signaling pathways. The individual components thusly modulated include growth factor receptors and transcription factors. The excessive generation of $O_2^-$ and $H_2O_2$ may be sufficient to propel the cellular redox balance to a more pro-oxidant state that favors oxidative damage and an apoptotic pathway.

UV radiation induces the generation of free radicals in biological tissues, such as skin. Among these free radicals, the superoxide anion ($O_2^-$) and the highly toxic hydroxyl radical ($OH^-$) cause tissue damage by reacting with biomolecules, such as lipids and proteins, and result in the formation of lipid peroxides.

Melatonin is an active participant in the antioxidative defense system of an organism. Studies suggest that melatonin is protective against free radical damage at physiological concentrations and is readily absorbed when administered via any route. Melatonin has proved effective in reducing oxidative damage in conditions where free radical involvement has been established, such as ionizing radiation. Resisting free radical damage is a feature of melatonin and melatonin can protect against a wide range of radical and reactive species damage.

It is believed that melatonin is an antioxidative protective agent against DNA damage and lipid peroxidation in vitro and in vivo. The mechanisms of melatonin inhibition of lipid peroxidation include the direct scavenging of the initiating radicals, especially $OH^{-1}$ and $ONOO^-$. Furthermore, a possible relationship exists between psoriasis, ROS, melatonin and its derivatives.

Moreover, indoles have long been known to possess chemical antioxidant properties and to protect against carcinogenesis. These functions have been attributed to the ability of indoles to react with free radicals and electrophiles. All indoleamines share a hetero-aromatic ring system of high electron-reactivity and only differ in the functional groups appended in the side chains. These side chains determine to a great extent the reactivity potency and efficiency of radical scavenging.

Consumers have long desired cosmetic and pharmaceutical compositions which provide cosmetically or pharmaceutically effective treatment or protection from the effects of free radicals. In response to this desire, antioxidants have been formulated through the years to protect from or prevent the harm associated with free radicals. Although melatonin is a radical scavenging agent, the reaction of melatonin and its analogues with ROS have not been fully studied, nor have the effects of melatonin or its metabolites and analogues upon psoriasis been evaluated. Similarly, there currently does not exist a satisfactory antioxidant derived from melatonin that provides all of the needed protection from the harmful effects of free radicals.

For this reason, there is a need in the art for compounds and compositions of melatonin derivatives which will adequately protect from the harmful effects of free radicals. The present subject matter addresses this need.

SUMMARY OF THE INVENTION

The present subject matter relates generally to compounds of formula I

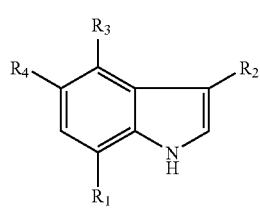

(I)

wherein:

$R_1$ is hydrogen, alkyl, alkenyl, alkoxy, or alkenoxy;

$R_2$ is hydrogen, $C_1$-$C_6$ alkyl($CH_2NO_2$)$_n$, $C_2$-$C_6$ alkenyl ($CH_2NO_2$)$_n$, $C_1$-$C_6$ alkyl-$NHCOCH_3$, $C_2$-$C_6$ alkenyl-$NHCOCH_3$, cycloalkyl, cycloalkenyl, aryl, heteroaryl, $C_1$-$C_6$ alkyl-$NH_2$, or $C_2$-$C_6$ alkenyl-$NH_2$;

$R_3$ is hydrogen, $CO(C_1$-$C_6$ alkyl), $CO(C_2$-$C_6$ alkenyl), $C_1$-$C_6$ alkyl-$NHCOCH_3$, $C_2$-$C_6$ alkenyl-$NHCOCH_3$, alkoxy, alkenoxy, $C_1$-$C_6$ alkyl($CH_2NO_2$)$_n$, $C_2$-$C_6$ alkenyl($CH_2NO_2$)$_n$, cycloalkyl, cycloalkenyl, aryl, or heteroaryl;

$R_4$ is alkoxy or alkenoxy; and

N represents 1, 2, or 3;

provided that:

when $R_2$ is $CH_2CH_2NHCOCH_3$ then $R_1$ and $R_3$ are not both hydrogen;

when $R_2$ is $CH_2CH_2NH_2$ and $R_1$ is hydrogen or alkoxy then $R_3$ is not hydrogen or alkoxy;

when $R_2$ is $CH_2CH_2NH_2$ and $R_3$ is hydrogen or alkoxy then $R_1$ is not hydrogen or alkoxy; and $R_1$, $R_2$, and $R_3$ are not all hydrogen.

In this regard, a preferred embodiment of the present subject matter relates to a compound of formula (I) wherein:

$R_1$ is hydrogen, alkyl, alkenyl, alkoxy, or alkenoxy;

$R_2$ is hydrogen, $C_1$-$C_6$alkyl($CH_2NO_2$)$_n$, $C_2$-$C_6$ alkenyl ($CH_2NO_2$)$_n$, $C_1$-$C_6$ alkyl-$NHCOCH_3$, $C_2$-$C_6$ alkenyl-$NHCOCH_3$, cycoalkyl, cycloalkenyl, aryl, heteroaryl, $C_1$-$C_6$ alkyl-$NH_2$, or $C_2$-$C_6$ alkenyl-$NH_2$;

$R_3$ is hydrogen, $CO(C_1$-$C_6$ alkyl), $CO(C_2$-$C_6$ alkenyl), $C_1$-$C_6$ alkyl-$NHCOCH_3$, $C_2$-$C_6$ alkenyl-$NHCOCH_3$, alkoxy, alkenoxy, $C_1$-$C_6$alkyl($CH_2NO_2$)$_n$, $C_2$-$C_6$ alkenyl($CH_2NO_2$)$_n$, cycloalkyl, cycloalkenyl, aryl, or heteroaryl;

$R_4$ is hydrogen, alkoxy, or alkenoxy; and n represents 1, 2, or 3; and wherein the compound is effective as an antioxidant.

DETAILED DESCRIPTION OF THE INVENTION

Definitions

As used herein, the terms "administering", "administration", and like terms refer to any method which, in sound medical or cosmetic practice, delivers the composition to a subject in such a manner as to provide a positive effect on a dermatological disorder, condition, or appearance. The compositions are preferably administered such that they cover the entire area to be treated. "Direct administration" refers to any method which, in sound medical or cosmetic practice, delivers the composition to a subject without the use of another composition, delivery agent, or device. "Indirect administration" refers to any method which, in sound medical or cosmetic practice, delivers the composition to a subject with the use of at least one other composition, delivery agent, or device.

As used herein, the term "alkenoxy" refers to branched or unbranched aliphatic ether radicals containing, without limitation, 2 to about 24 carbon atoms and at least one double bond. Likewise, as used herein, "alkoxy" refers to branched or unbranched aliphatic ether radicals containing, without limitation, 1 to about 24 carbon atoms. The term "lower alkenoxy" intends an alkenoxy group of about two to about six carbon atoms, preferably about two to about four carbon atoms, such as without limitation ethenoxy, propenoxy, isopropenoxy, n-butenoxy, isobutenoxy, sec-butenoxy, and tert-butenoxy.

As used herein, the term "alkenyl" refers to a branched or unbranched hydrocarbon group containing, without limitation, about 2 to about 24 carbon atoms and at least one double bond, such as ethenyl, n-propenyl, isopropenyl, n-butenyl, isobutenyl, octenyl, decenyl, and the like. Preferably, alkenyl groups herein contain about 2 to about 12 carbon atoms. The term "lower alkenyl" intends an alkenyl group of about two to about six carbon atoms, preferably two to four carbon atoms. "Substituted alkenyl" refers to an alkenyl group substituted with one or more substituent groups, and the terms "heteroatom-containing alkenyl" and "heteroalkenyl" refer to an alkenyl group in which at least one carbon atom is replaced with a heteroatom. "Heteroatom-containing alkenyl" and "heteroalkenyl" are used interchangeably herein.

As used herein, the term "alkoxyl" refers to branched or unbranched aliphatic ether radicals containing, without limitation, about 1 to about 24 carbon atoms. Preferably, alkoxy groups herein contain about 1 to about 12 carbon atoms. The term "lower alkoxyl" intends an alkoxy group of about one to about six carbon atoms, preferably about one to about four carbon atoms, such as methoxy, ethoxy, propoxy, isopropoxy, n-butoxy, isobutoxy, sec-butoxy, and tert-butoxy.

As used herein, the term "alkyl" refers to a branched or unbranched saturated hydrocarbon group containing, without limitation, about 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl, and the like. Preferably, alkyl groups herein contain about 1 to about 12 carbon atoms. The term "lower alkyl" intends an alkyl group of about one to about six carbon atoms, preferably about one to, about four carbon atoms. "Substituted alkyl" refers to alkyl substituted with one or more substituent groups, and the terms "heteroatom-containing alkyl" and "heteroalkyl" are used interchangeably herein and refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl or lower alkyl groups.

As used herein, the term "amide" means a group represented by the formula —CO—NH$_2$.

As used herein, the term "aryl" refers to an aromatic substituent containing a single aromatic ring or multiple aromatic rings that are fused together, linked covalently, or linked to a common group, for example, a methylene or ethylene moiety. The common linking group may also be a carbonyl as in benzophenone, an oxygen atom as in diphenylether, or a nitrogen atom as in diphenylamine. Preferred aryl groups contain one aromatic ring and are referred to as "monocyclic aryl." "Substituted aryl" refers to an aryl moiety substituted with one or more substituent groups, and the terms "heteroatom-containing aryl" and "heteroaryl" are used interchangeably and refer to an aryl group in which at least one carbon atom is replaced with a heteroatom.

As used herein, the terms "carriers" or "vehicles" are used interchangeably and refer to pharmaceutically acceptable carrier materials suitable for topical, oral, or other active administration. Carriers and vehicles useful herein include any such materials known in the art that are nontoxic and do not interact with other components of the composition in a deleterious manner.

As used herein, the phrases an "effective amount" or a "therapeutically effective amount" of an active agent or ingredient, or pharmaceutically active agent or ingredient, are used interchangeably and refer to an amount of the pharmaceutically active agent sufficient enough to have a desired effect on the area of application. Accordingly, these amounts are sufficient to modify the skin disorder, condition, or appearance to be treated, but the amounts are low enough to avoid serious side effects, within the scope of sound medical or dermatological advice. A therapeutically effective amount of the pharmaceutically active agent will cause a substantial relief of symptoms when applied repeatedly over time. Effective amounts of the pharmaceutically active agent will vary based on a number of factors, which include without limitation, the particular condition or conditions being treated, the severity of the condition, the duration of the treatment, the specific components of the composition being used, and other such factors.

As used herein, the phrase "having the formula" or "having the structure" is not intended to be limiting and is used in the same way that the term "comprising" is commonly used".

As used herein, the term "heteroatom-containing" refers to a molecule or molecular fragment in which one or more carbon atoms is replaced with an atom other than carbon. The atom that replaces the carbon atom is referred to as a "heteratom". Suitable replacement atoms include, without limitation, nitrogen, oxygen, sulfur, phosphorus, or silicon. For example, the term "heteroalkyl" refers to an alkyl substituent that contains a heteroatom, the term "heterocyclic" refers to a cyclic substituent that contains a heteroatom, the term "heteroaryl" refers to an aryl substituent that contains a heteroatom". When the term "heteroatom-containing" appears prior to a list of possible heteroatom-containing groups, it is intended that the term apply to every member of that group. For a non-limiting example, the phrase "heteroatom-containing alkyl, alkenyl, and alkynyl" is to be interpreted as "heteroatomcontaining alkyl, heteroatom-containing alkenyl, and heteroatom-containing alkynyl".

As used herein, the term "mammal" refers to any warm blooded animal such as, but not limited to, companion animals such as cats and dogs, primates such as monkeys and chimpanzees, and livestock animals such as horses, cows, pigs, and sheep. Preferably, the mammal is human.

As used herein, the phrase "pharmaceutically acceptable," refers to a compound that is not biologically or otherwise undesirable, i.e., the compound may be incorporated into a formulation herein and administered to a patient without causing any undesirable biological effects or interacting in a deleterious manner with any of the other components of the formulation in which it is contained. A "pharmacologically active" compound refers to an active agent as defined below, or to an analog or derivative thereof having the same type of pharmacological activity as the parent compound.

As used herein, the phrase "pharmaceutically acceptable salts" refers to salts of certain ingredient(s) which possess the same activity as the unmodified compound(s) and which are neither biologically nor otherwise undesirable. A salt can be formed with, for example, organic or inorganic acids. Non-limiting examples of suitable acids include acetic acid, acetylsalicylic acid, adipic acid, alginic acid, ascorbic acid, aspartic acid, benzoic acid, benzenesulfonic acid, bisulfic acid, boric acid, butyric acid, camphoric acid, camphorsulfonic acid, carbonic acid, citric acid, cyclopentanepropionic acid, digluconic acid, dodecylsulfic acid, ethanesulfonic acid, formic acid, fumaric acid, glyceric acid, glycerophosphoric acid, glycine, glucoheptanoic acid, gluconic acid, glutamic acid, glutaric acid, glycolic acid, hemisulfic acid, heptanoic acid, hexanoic acid, hippuric acid, hydrobromic acid, hydrochloric acid, hydroiodic acid, hydroxyethanesulfonic acid, lactic acid, maleic acid, malic acid, malonic acid, mandelic acid, methanesulfonic acid, mucic acid, naphthylanesulfonic acid, naphthylic acid, nicotinic acid, nitrous acid, oxalic acid, pelargonic, phosphoric acid, propionic acid, saccharin, salicylic acid, sorbic acid, succinic acid, sulfuric acid, tartaric acid, thiocyanic acid, thioglycolic acid, thiosulfuric acid, tosylic acid, undecylenic acid, and naturally and synthetically derived amino acids.

Non-limiting examples of base salts include ammonium salts; alkali metal salts, such as sodium and potassium salts; alkaline earth metal salts, such as calcium and magnesium salts; salts with organic bases, such as dicyclohexylamine salts; methyl-D-glucamine; and salts with amino acids, such as arginine, lysine, and so forth. Also, the basic nitrogen-containing groups can be quaternized with such agents as lower alkyl halides, such as methyl, ethyl, propyl, and butyl chlorides, bromides, and iodides; dialkyl sulfates, such as dimethyl, diethyl, dibutyl, and diamyl sulfates; long chain halides, such as decyl, lauryl, myristyl, and stearyl chlorides, bromides, and iodides; asthma halides, such as benzyl and phenethyl bromides; and others. Water or oil-soluble or dispersible products are thereby obtained. Preferred salts include acetate, butyrate, hemisuccinate and phosphate.

As used herein, the phrase "pharmacologically active agent," "pharmacologically active base," and "active agent" are used interchangeably herein to refer to a basic compound or composition of matter that, when administered to a human patient, induces a desired pharmacologic and/or physiologic effect by local and/or systemic action. In a non-limiting example, topical administration of an "active agent" leads to moisturizing the skin or repairing or maintaining skin barrier function. Also included are derivatives and analogs of those compounds or classes of compounds specifically mentioned that also induce the desired effect.

As used herein, the phrase "skin protectant" refers to an ingredient or ingredients that have the ability to repair interstitial lipid layers, provide lipid restoration, provide skin barrier restoration, increase water amounts intercellularly within at least one skin layer, and/or result in improvements in skin integrity.

As used herein, "substituted" refers to at least one hydrogen atom bound to a carbon atom in a chemical moiety which is replaced with one or more substituents that are functional groups. Non-limiting examples of functional groups include hydroxyl, alkoxy, thio, amino, halo, and the like.

As used herein, the phrase "therapeutic composition" refers to a composition which, upon administration, demonstrates a therapeutic affect upon a mammal.

As used herein, the phrase "topical administration" is used in its conventional sense to mean delivery of a pharmacologically active agent to the skin or mucosal tissue. Topical administration of a pharmacologically active agent often results in moisturizing the skin or repairing or maintaining skin barrier function.

Other terms as used herein are meant to be defined by their well-known meanings in the art.

Derivatives of Melatonin

Melatonin scavenges $H_2O_2$ resulting in the formation of $N^1$-acetyl-$N^2$-formyl-5-methoxykynuramine (AFMK). In addition, there is a cascade which could increase the efficiency of melatonin as an antioxidant, since the products formed in the cascade may also be free radical scavengers. Furthermore, AFMK often functions as a potent antioxidant, reducing lipid peroxidation as well as DNA damage.

Accordingly, a preferred aspect of the present subject matter relates to melatonin derivatives which act as antioxidants. In particular, the present subject matter preferably relates to compounds which protect from or prevent the harmful effects of free radicals. Preferably, the present subject matter is direct to melatonin derivatives which are effective as antioxidants.

The preferred melatonin derivatives of the present subject matter are indoles. The exact nature of hydroxy or methoxy substitution, as well as the position (4, 5, 6, or 7) of the substituents, in the indole may affect the antioxidant and anti-psoriatic activities of the indole.

In one preferred embodiment, the present compounds relate to melatonin derivatives of formula (I):

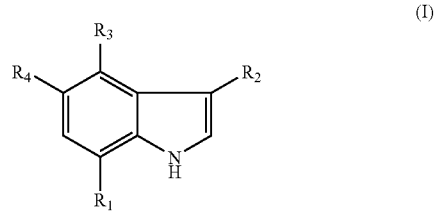

wherein
  $R_1$ is hydrogen, alkyl, alkenyl, alkoxy, or alkenoxy;
  $R_2$ is hydrogen, $C_1$-$C_6$ alkyl($CH_2NO_2$)$_n$, $C_2$-$C_6$ alkenyl($CH_2NO_2$)$_n$, $C_1$-$C_6$ alkyl-NHCOCH$_3$, $C_2$-$C_6$ alkenyl-NHCOCH$_3$, cycloalkyl, cycloalkenyl, aryl, heteroaryl, $C_1$-$C_6$ alkyl-NH$_2$, or $C_2$-$C_6$ alkenyl-NH$_2$;
  $R_3$ is hydrogen, CO($C_1$-$C_6$ alkyl), CO($C_2$-$C_6$ alkenyl), $C_1$-$C_6$ alkyl-NHCOCH$_3$, $C_2$-$C_6$ alkenyl-NHCOCH$_3$, alkoxy, alkenoxy, $C_1$-$C_6$ alkyl($CH_2NO_2$)$_n$, $C_2$-$C_6$ alkenyl($CH_2NO_2$)$_n$, cycloalkyl, cycloalkenyl, aryl, or heteroaryl;
  $R_4$ is alkoxy or alkenoxy; and
  n represents 1, 2, or 3;
  provided that:
    when $R_2$ is $CH_2CH_2NHCOCH_3$ then $R_1$ and $R_3$ are not both hydrogen;
    when $R_2$ is $CH_2CH_2NH_2$ and $R_1$ is hydrogen or alkoxy then $R_3$ is not hydrogen or alkoxy;
    when $R_2$ is $CH_2CH_2NH_2$ and $R_3$ is hydrogen or alkoxy then $R_1$ is not hydrogen or alkoxy; and
    $R_1$, $R_2$, and $R_3$ are not all hydrogen.

Another presently preferred compound is a compound according to formula (I) wherein:
  $R_1$ is hydrogen, $C_1$-$C_6$ alkyl, $C_2$-$C_6$ alkenyl, $C_1$-$C_6$ alkoxy, or $C_2$-$C_6$ alkenoxy;
  $R_2$ is $C_1$-$C_6$ alkyl($CH_2NO_2$)$_n$ or $C_2$-$C_6$ alkenyl($CH_2NO_2$)$_n$;
  $R_3$ is hydrogen, $C_1$-$C_6$ alkoxy, or $C_2$-$C_6$ alkenoxy;
  $R_4$ is $C_1$-$C_6$ alkoxy or $C_2$-$C_6$ alkenoxy; and
  n is 1, 2, or 3.

Yet another presently preferred compound is a compound according to formula (I) wherein:
  $R_1$ is hydrogen, $C_1$-$C_6$ alkyl, $C_2$-$C_6$ alkenyl, $C_1$-$C_6$ alkoxy, or $C_2$-$C_6$ alkenoxy;
  $R_2$ is $C_1$-$C_6$ alkyl-NHCOCH$_3$ or $C_2$-$C_6$ alkenyl-NHCOCH$_3$;
  $R_3$ is hydrogen, CO($C_1$-$C_6$ alkyl), CO($C_2$-$C_6$ alkenyl), $C_1$-$C_6$ alkoxy, or $C_2$-$C_6$ alkenoxy; and
  $R_4$ is $C_1$-$C_6$ alkoxy or $C_2$-$C_6$ alkenoxy;
  provided that:

when $R_2$ is $CH_2CH_2NHCOCH_3$ then $R_1$ and $R_3$ are not both hydrogen.

A further presently preferred compound is a compound according to formula (I) wherein:
$R_1$ is hydrogen, $C_1$-$C_6$ alkyl, $C_2$-$C_6$ alkenyl, $C_1$-$C_6$ alkoxy, or $C_2$-$C_6$ alkenoxy;
$R_2$ is hydrogen;
$R_3$ is $C_1$-$C_6$ alkyl-$NHCOCH_3$ or $C_2$-$C_6$ alkenyl-$NHCOCH_3$; and
$R_4$ is $C_1$-$C_6$ alkoxy or $C_2$-$C_6$ alkenoxy.

Another presently preferred compound is a compound according to formula (I) wherein:
$R_1$ is hydrogen, $C_1$-$C_6$ alkyl, $C_2$-$C_6$ alkenyl, $C_1$-$C_6$ alkoxy, or $C_2$-$C_6$ alkenoxy;
$R_2$ is $C_1$-$C_6$ alkyl-$NH_2$ or $C_2$-$C_6$ alkenyl-$NH_2$;
$R_3$ is hydrogen, $C_1$-$C_6$ alkoxy, or $C_2$-$C_6$ alkenoxy; and
$R_4$ is $C_1$-$C_6$ alkoxy or $C_2$-$C_6$ alkenoxy;
provided that:
when $R_2$ is $CH_2CH_2NH_2$ and $R_1$ is hydrogen or $C_1$-$C_6$ alkoxy then $R_3$ is not hydrogen or $C_1$-$C_6$ alkoxy;
when $R_2$ is $CH_2CH_2NH_2$ and $R_3$ is hydrogen or $C_1$-$C_6$ alkoxy then $R_1$ is not hydrogen or $C_1$-$C_6$ alkoxy.

A further presently preferred compound is a compound according to formula (I) wherein:
$R_1$ is hydrogen, $C_1$-$C_6$ alkyl, $C_2$-$C_6$ alkenyl, $C_1$-$C_6$ alkoxy, or $C_2$-$C_6$ alkenoxy;
$R_2$ is hydrogen, $C_1$-$C_6$ alkoxy, or $C_2$-$C_6$ alkenoxy;
$R_3$ is $C_1$-$C_6$ alkyl$(CH_2NO_2)_n$ or $C_2$-$C_6$ alkenyl$(CH_2NO_2)_n$; and
$R_4$ is $C_1$-$C_6$ alkoxy or $C_2$-$C_6$ alkenoxy.

Yet another presently preferred compound is a compound according to formula (I) wherein:
$R_1$ is hydrogen, $C_1$-$C_6$ alkyl, $C_2$-$C_6$ alkenyl, $C_1$-$C_6$ alkoxy, or $C_2$-$C_6$ alkenoxy;
$R_2$ is hydrogen, $C_1$-$C_6$ alkoxy, or $C_2$-$C_6$ alkenoxy;
$R_3$ is cycloalkyl, cycloalkenyl, aryl, or heteroaryl; and
$R_4$ is $C_1$-$C_6$ alkoxy or $C_2$-$C_6$ alkenoxy.

In a particularly preferred embodiment, $R_2$ is a heteroaryl comprising nitrogen heteroatoms. In further particularly preferred compounds the heteroaryl is a pyrazole.

Another presently preferred compound is a compound according to formula (I) wherein:
$R_1$ is hydrogen, $C_1$-$C_6$ alkyl, $C_2$-$C_6$ alkenyl, $C_1$-$C_6$ alkoxy, or $C_2$-$C_6$ alkenoxy;
$R_2$ is cycloalkyl, cycloalkenyl, aryl, or heteroaryl;
$R_3$ is hydrogen, $C_1$-$C_6$ alkoxy, or $C_2$-$C_6$ alkenoxy; and
$R_4$ is $C_1$-$C_6$ alkoxy or $C_2$-$C_6$ alkenoxy.

In a preferred embodiment $R_2$ is a heteroaryl comprising nitrogen heteroatoms. In a particularly preferred embodiment, the heteroaryl is a pyrazole.

Further particularly preferred compounds of the present subject matter are the following compounds:
1. a compound of formula I wherein $R_1$ is hydrogen, $R_2$ is $CH(CH_2NO_2)_2$, $R_3$ is hydrogen, and $R_4$ is $OCH_3$, thereby forming the compound of the formula

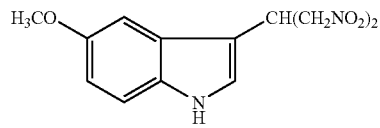

which is known by the name of 5-Methoxy-3-bis(2-nitromethyl)methylindole;

2. a compound of formula I wherein $R_1$ is hydrogen, $R_2$ is $CH_2CH_2NHCOCH_3$, $R_3$ is $COCH_3$, and $R_4$ is $OCH_3$, thereby forming the compound of the formula

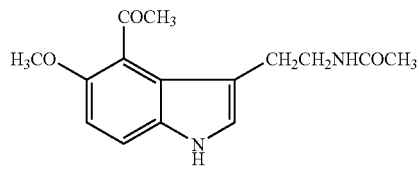

which is known by the name of 4-Acetylmelatonin;

3. a compound of formula I wherein $R_1$ is hydrogen, $R_2$ is a moiety of the formula

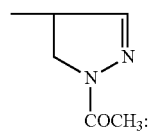

$R_3$ is hydrogen, and $R_4$ is $OCH_3$, thereby forming the compound of the formula

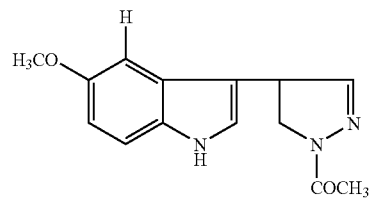

which is known by the name of 1-Acetyl-4,5-dihydro-4-(5'-methoxyindol-3'-yl)-1H-pyrazole;

4. a compound of formula I wherein $R_1$ is $OCH_3$, $R_2$ is a moiety of the formula

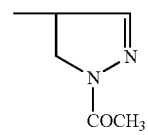

$R_3$ is hydrogen, and $R_4$ is $OCH_3$, thereby forming the compound of the formula

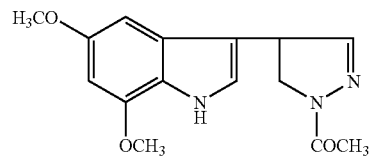

which is known by the name of 1-Acetyl-4,5-dihydro-4-(5',7'-dimethoxyindol-3'-yl)-1H-pyrazole;

5. a compound of formula I wherein $R_1$ is hydrogen, $R_2$ is a moiety of the formula

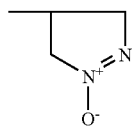

$R_3$ is hydrogen, and $R_4$ is $OCH_3$, thereby forming the compound of the formula

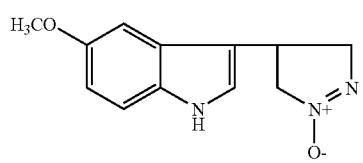

which is known by the name of 4,5-Dihydro-4-(5'-methoxyindol-3'-yl)-3H-pyrazole-N1-oxide;

6. a compound of formula I wherein $R_1$ is hydrogen, $R_2$ is $CH_2CH_2NHCOCH_3$, $R_3$ is $OCH_3$, and $R_4$ is $OCH_3$, thereby forming the compound of the formula

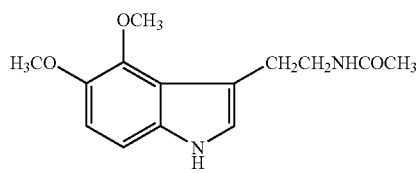

which is known by the name of 4-Methoxymelatonin;

7. a compound of formula I wherein $R_1$ is hydrogen, $R_2$ is $CH=CHNO_2$, $R_3$ is $OCH_3$, and $R_4$ is $OCH_3$, thereby forming the compound of the formula

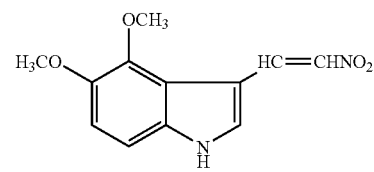

which is known by the name of 4,5-Dimethoxy-3-(2-nitroethenyl)-indole;

8. a compound of formula I wherein $R_1$ is hydrogen, $R_2$ is a moiety of the formula

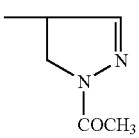

$R_3$ is $OCH_3$, and $R_4$ is $OCH_3$, thereby forming the compound of the formula

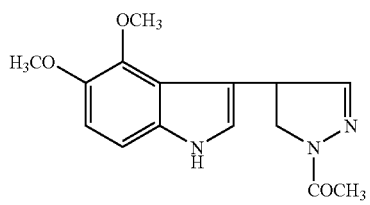

which is known by the name of 1-Acetyl-4,5-dihydro-4-(4',5'-dimethoxyindol-3'-yl)-1H-pyrazole;

9. a compound of formula I wherein $R_1$ is $OCH_3$, $R_2$ is hydrogen $R_3$ is $CH_2CH_2NHCOCH_3$, and $R_4$ is $OCH_3$, thereby forming the compound of the formula

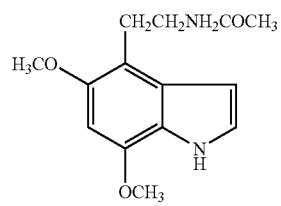

which is known by the name of 4-[2(N-Acetyl)-aminoethyl]-5,7-dimethoxyindole;

10. a compound of formula I wherein $R_1$ is $OCH_3$, $R_2$ is $CH(CH_2NO_2)_2$, $R_3$ is hydrogen, and $R_4$ is $OCH_3$, thereby forming the compound of the formula

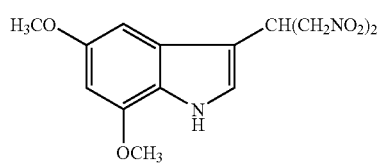

which is known by the name of 5,7-Dimethoxy-3-[bis(2-nitromethyl)methyl]indole;

11. a compound of formula I wherein $R_1$ is hydrogen, $R_2$ is $CH(CH_2NO_2)_2$, $R_3$ is $OCH_3$, and $R_4$ is $OCH_3$, thereby forming the compound of the formula

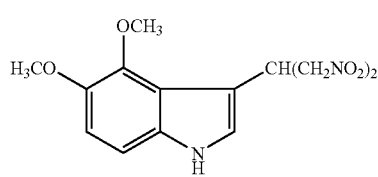

which is known by the name of 4,5-Dimethoxy-3-[bis(2-nitromethyl)methyl]indole;

12. a compound of formula I wherein $R_1$ is $OCH_3$, $R_2$ is H, $R_3$ is $CH(CH_2NO_2)_2$, and $R_4$ is $OCH_3$, thereby forming the compound of the formula

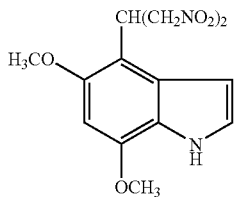

which is known by the name of 5,7-Dimethoxy-4-bis(nitromethyl)methylindole;

13. a compound of formula I wherein $R_1$ is $OCH_3$, $R_2$ is H, $R_3$ is

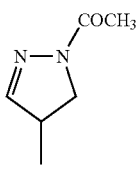

and $R_4$ is $OCH_3$, thereby forming the compound of the formula

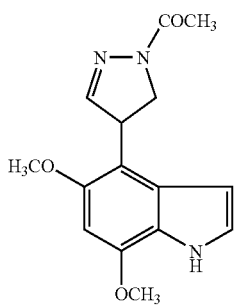

which is known by the name of 1-Acetyl-4,5-dihydro-4-(5',7'-dimethoxyindole-4'-yl)-1H-pyrazole;

14. A compound of the name 5,7-Dimethoxy-4-{2'-nitro-1'-(nitromethyl)ethyl}indole, the synthesis of which is described in Example 12;

15. A compound of the name 1-Acetyl-4,5-dihydro-4-(5', 7'-dimethoxyindol-4'-yl)-1H-pyrazole, the synthesis of which is described in Example 13;

or enantiomers thereof; and a pharmaceutically acceptable salt or derivative thereof.

Methods of Treatment

Skin possesses antioxidant defense mechanisms in the form of specific enzymes in the keratinocytes. One such enzyme is superoxide dismutase (SOD). Under UV irradiation, free radicals deplete the endogenous enzymatic and non-enzymatic antioxidants of the skin, leaving it vulnerable to oxidative stress. Therefore, supplementation of antioxidants to the skin may limit or prevent UV-induced skin damage or cancer. In addition, the various effects of melatonin indicate that it plays a role in modulating acute inflammation due to its free radical scavenger and antioxidant properties.

Accordingly, a preferred aspect of the present subject matter relates to the use of melatonin derivatives compositions containing the same as antioxidants. In particular, the present subject matter preferably relates to compositions which protect from or prevent the harmful effects of free radicals.

Yet another preferred aspect of the present subject matter is drawn to a method of using the subject compounds as an antioxidant. A further aspect of the present subject matter is a nutritional, pharmaceutical or cosmetic composition comprising one or more of the subject compositions and a pharmaceutically acceptable carrier. In yet another preferred aspect, the method comprises protecting a mammal against the effects of free radicals by administering to a mammal in need thereof an amount of a composition comprising one or more of the preferred compounds which is effective to protect against the effect of said free radicals. Another preferred aspect of the invention is the use of one or more of the compound(s) of the invention in the manufacture of a medicament for protecting a mammal against the effects of free radicals. Another preferred aspect of the invention is one or more of the compound(s) of the invention for use in protecting a mammal against the effects of free radicals.

Another presently preferred aspect is drawn to a method comprising protecting a mammal against the effects of free radicals by administering to a mammal in need thereof an amount of one or more of an antioxidant subject compounds which is effective to protect against the effect of said free radicals. Another preferred aspect of the invention is the use of one or more of the an antioxidant subject compounds which is effective to protect against the effect of free radicals in the manufacture of a medicament for protecting a mammal against the effects of free radicals. Another preferred aspect of the invention is one or more of the an antioxidant subject compounds which is effective to protect against the effect of free radicals for use in protecting a mammal against the effects of free radicals.

Melatonin is efficiently absorbed by way of various administration routes and has a unique distribution profile due to it being freely distributed throughout all subcellular compartments. Melatonin crosses biological barriers, such as the blood brain barrier and the placenta, with ease. In addition, melatonin has a high lipid solubility which allows for topical administration. Accordingly, it would be expected that the present melatonin derivatives would possess similar attributes.

Yet another preferred aspect of the present subject matter is directed to a method of treating a free radical induced disease state selected from the group consisting of emphysema, viral hepatitis, cancer, tuberculosis, psoriasis, atherosclerosis, systemic lupus erythematosus, and heightened LDL cholesterol comprising administrating a presently preferred compound or composition containing one said preferred compound to a mammal in need thereof. Another preferred aspect of the invention is the use of one or more of the compound(s) of the invention in the manufacture of a medicament for treating a free radical induced disease state selected from the group consisting of emphysema, viral hepatitis, cancer, tuberculosis, psoriasis, atherosclerosis, systemic lupus erythematosus, and heightened LDL cholesterol. Another preferred aspect of the invention is one or more of the compound(s) of the invention for use in treating a free radical induced disease state selected from the group consisting of emphysema, viral hepatitis, cancer, tuberculosis, psoriasis, atherosclerosis, systemic lupus erythematosus, and heightened LDL cholesterol. A further preferred method comprises treating a patient afflicted with a chronic inflammatory disease by administering a therapeutically effective amount of one or more of the presently preferred compounds to a mammal in need thereof. Another preferred aspect of the invention is the use of one or more of the compound(s) of the invention in the manufacture of a medicament for treating a patient afflicted with a chronic inflammatory disease. Another preferred aspect of the invention is one or more of the compound(s) of the invention for use in treating a patient afflicted with a chronic inflammatory disease.

The above mentioned melatonin derivatives and compositions containing these derivatives as active agents act as effective antioxidants and free radical scavengers. Therefore, the above-mentioned melatonin derivatives are effective at treating the above free radical induced disease states.

Another preferred aspect is directed to a method of prolonging the shelf life of cosmetic and personal care items that are susceptible to rancidity comprising mixing one or more preferred compounds with a cosmetic or personal care item.

Preferred antioxidant compounds of the present subject matter useful in these methods include compounds of formula (I) wherein:

$R_1$ is hydrogen, alkyl, alkenyl, alkoxy, or alkenoxy;

$R_2$ is hydrogen, $C_1$-$C_6$ alkyl($CH_2NO_2$)$_n$, $C_2$-$C_6$ alkenyl ($CH_2NO_2$)$_n$, $C_1$-$C_6$ alkyl-$NHCOCH_3$, $C_2$-$C_6$ alkenyl-$NHCOCH_3$, cycloalkyl, cycloalkenyl, aryl, heteroaryl, $C_1$-$C_6$ alkyl-$NH_2$, or $C_2$-$C_6$ alkenyl-$NH_2$;

$R_3$ is hydrogen, CO($C_1$-$C_6$ alkyl), CO($C_2$-$C_6$ alkenyl), $C_1$-$C_6$ alkyl-$NHCOCH_3$, $C_2$-$C_6$ alkenyl-$NHCOCH_3$, alkoxy, alkenoxy, $C_1$-$C_6$ alkyl($CH_2NO_2$)$_n$, $C_2$-$C_6$ alkenyl($CH_2NO_2$)$_n$, cycloalkyl, cycoalkenyl, aryl, or heteroaryl;

$R_4$ is hydrogen, alkoxy, or alkenoxy; and n represents 1, 2, or 3.

In yet another preferred embodiment, an antioxidant compound of the present subject matter is present as an active agent along with a pharmaceutically acceptable carrier in a nutritional, pharmaceutical or cosmetic composition.

In still another particularly preferred method, an antioxidant compound of the present subject matter is administered to protect a mammal against the effects of free radicals.

Administration of Melatonin Derivatives

The present subject matter also features the formulation of the preferred melatonin derivatives of general formula (I) as anti-free-radical active agents into cosmetic compositions for improving the appearance of skin, scalp, or hair.

The preferred compositions are preferably cosmetic compositions for controlling the damage caused by free radicals to skin, scalp or hair. Thus, the present subject matter also features a cosmetic treatment or regimen which entails improving the appearance of skin, scalp and/or hair, by topically applying to the skin and/or the scalp and/or the hair a composition comprising, as an anti-free-radical active agent, an effective amount of a preferred melatonin derivative as described herein.

In addition, the preferred compositions may also be dermatological compositions and, in this event, the present subject matter also includes the formulation of the preferred melatonin derivatives as described herein into pharmaceutical compositions for the dermatological treatment of damage caused by free radicals.

The cosmetic or dermatological compositions into which the preferred melatonin derivatives are formulated may exist in any pharmaceutical form for topical, oral, or other application which is normal in this art. The preferred compositions may be in any form, including without limitation, an aqueous solution, an oily suspension, a dispersion in a lotion, emulsions of liquid or semi-liquid consistency, obtained by dispersing a fatty phase in an aqueous phase (oil-in-water) or, conversely, by dispersing an aqueous phase in a fatty phase (water-in-oil), creams, gels, tablets, capsules, microcapsules or microparticles, or vesicle dispersions of ionic and/or non-ionic type. Formulating compositions in the above forms is well-known in the art.

The compositions according to the present subject matter may also be in the form of solid preparations, including without limitation, cleansing soaps or bars.

The preferred compositions may also be packaged in the form of an aerosol composition also comprising a propellant under pressure.

The preferred cosmetic or dermatological composition may also contain additives and adjuvants that are common in the cosmetic or dermatological arts, such as hydrophilic or lipophilic gelling agents, hydrophilic or lipophilic additives, preservatives, antioxidants, solvents, fragrances, fillers, screening agents, odor-absorbers and dyestuffs and colorants. The amounts of these various additives and adjuvants are those conventionally used in these fields, Insofar as they do not interfere with the activity of the subject melatonin derivatives, the compositions according to the present subject matter may contain other active agents intended, In particular, for the prevention and/or treatment of skin conditions/afflictions.

Pharmaceutically Acceptable Topical Carriers

The presently preferred compositions in the described methods of treatment use a pharmaceutically acceptable topical carrier to administer melatonin derivative compositions to the skin of a patient in need thereof.

Preferred pharmaceutically acceptable topical carriers can include at least one substance which forms lamellar structures with water, preferred, non-limiting examples of substances which forms lamellar structures with water useful herein include monoglycerides, diglycerides, distilled medium-chain monoglycerides, sphinoglipids, phospholipids, fatty alcohols, fatty acids, soaps, mono-esters of fatty acids, di-esters of fatty acids, sucrose, glucose, sterols, mono-esters of fatty acids and sterols, di-esters of fatty acids and sterols, glycol derivatives of sterols, derivatives thereof, metabolites thereof, and mixtures thereof.

In another preferred embodiment, the present topical carriers can further include at least one component selected from the group consisting of S-adenosylmethionine, acetyl-choline, choline, glycophospocholine, phosphatidylcholine, lysophospatidylcholine, carnatine, acylcarnatine, sphingomyeline, derivatives thereof, metabolites thereof, and mixtures thereof.

In still another preferred embodiment, the present topical carriers contain and/or are formed as a hydrophilic medium.

Dermatologically Acceptable Excipients

The preferred compositions discussed herein can additionally comprise at least one dermatologically acceptable excipient commonly known to those of ordinary skill in the art as useful in topical compositions. Preferred, non-limiting examples of dermatologically acceptable excipients useful in these methods are those selected from the group consisting of moisturizers, preservatives, gelling agents, colorants or pigments, radical scavengers, surfactants, emulsifiers, pH modifiers, chelating agents, derivatives thereof, and mixtures thereof.

Moisturizers

The presently preferred compositions may optionally further contain at least one moisturizer. Preferably, the presently preferred methods can comprise about 0.01% to about 10% by weight of at least one moisturizer. Preferred non-limiting examples of moisturizers include glycerin, pentylene glycol, butylene glycol, polyethylene glycol, sodium pyrrolidone carboxylate, alpha-hydroxy acids, beta-hydroxy acids, polyhydric alcohols, ethoxylated and propoxylated polyols, polyols, polysaccharides, panthenol, hexylene glycol, propylene glycol, dipropylene glycol, sorbitol, derivatives thereof, and mixtures thereof.

Preservatives

The presently preferred compositions may optionally further contain at least one preservative. Preferred non-limiting examples of preservatives include glycerol, sorbitol, benzyl alcohol, methyl paraben, ethyl paraben, derivatives thereof, and mixtures thereof.

The preservative is preferably present in an amount of about 0.1% to about 2.5% by weight of the overall weight of the composition.

Gelling Agents

The presently preferred compositions may optionally further contain a gelling agent. Preferred non-limiting examples of gelling agents include various cellulose agents, such as cellulosic polymers, methylcellulose, hydroxyethylcellulose, hydroxypropylcellulose and hydroxypropylmethylcellulose. Additional, non-limiting examples of gelling agents include gum arabic, gum tragacanth, locust bean gum, guar gum, xanthan gum, cellulose gum, sodium carbomer, carbomer, polyacrylic polymers, derivatives thereof, and mixtures thereof. Other suitable gelling agents which may be useful in the present compositions include aqueous gelling agents, such as neutral, anionic, and cationic polymers, derivatives thereof, and mixtures thereof.

Exemplary polymers which may be useful in the preferred compositions in this regard include carboxy vinyl polymers, such as carboxypolymethylene. Additionally preferred gelling agents include Carbopol® and Carbomer® polymers (i.e. polyacrylic polymers) such as is available from Noveon Inc., Cleveland, Ohio. Other preferred gelling agents include Pemulen® polymer (i.e. polyacrylic polymer) such as is available from Noveon Inc., Cleveland, Ohio.

The gelling agent is preferably present in the instant compositions in an amount of from about 0.01% to about 10%, more preferably from about 0.1% to about 5%, and most preferably from about 0.1% to about 2%, by weight.

Emulsifiers

The presently preferred compositions may optionally further contain an emulsifier. Preferably, the presently preferred compositions comprise about 0.05% to about 15% by weight, and more preferably from about 0.5% to about 10% by weight of at least one emulsifier. In a preferred embodiment, the emulsifier can be a polyacrylic emulsifier.

Preferred, non-limiting examples of specific emulsifiers useful in this regard include glycol esters, fatty acids, fatty alcohols, fatty acid glycol esters, fatty esters, fatty ethers, esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, derivatives thereof, and mixtures thereof.

Any other emulsifiers known to those of skill in the art as useful in the formation of topical compositions are further contemplated herein.

pH Modifiers

The presently preferred compositions may optionally further contain a pH modifier. Preferably, the presently preferred compositions comprise about 0.001% to about 1% by weight of a pH modifier. Preferred non-limiting examples of pH modifiers include inorganic hydroxides, inorganic oxides, inorganic salts of weak acids, derivatives thereof, and mixtures thereof.

Preferred, non-limiting examples of inorganic hydroxides useful as pH modifiers include ammonium hydroxide, alkali metal hydroxide, alkaline earth metal hydroxides, derivatives thereof, and mixtures thereof.

Preferred inorganic hydroxides useful as pH modifiers include ammonium hydroxide, monovalent alkali metal hydroxides such as sodium hydroxide and potassium hydroxide, divalent alkali earth metal hydroxides such as calcium hydroxide and magnesium hydroxide, derivatives thereof, and mixtures thereof.

Preferred, non-limiting examples of inorganic oxides useful as pH modifiers include magnesium oxide, calcium oxide, derivatives thereof, and mixtures thereof.

Preferred, non-limiting examples of inorganic salts of weak acids useful as pH modifiers include ammonium phosphate (dibasic), alkali metal salts of weak acids such as sodium acetate, sodium borate, sodium metaborate, sodium carbonate, sodium bicarbonate, sodium phosphate (tribasic), sodium phosphate (dibasic), potassium carbonate, potassium bicarbonate, potassium citrate, potassium acetate, potassium phosphate (dibasic), potassium phosphate (tribasic), alkaline earth metal salts of weak acids such as magnesium phosphate and calcium phosphate, derivatives thereof, and mixtures thereof.

Humectants

The presently preferred compositions may optionally further contain a humectant. Preferred, non-limiting examples of humectants useful in this regard include sorbitol, sorbitol syrup, E965 maltitol, maltitol, maltitol syrup, E1200 polydextrose, E1518 glyceryl triacetate, triacetin, glyceryl triacetate, 1,2,3-propanetriyl triacetate, 1,2,3-propanetriol triacetate, triacetylglycerol, E1520 propylene glycol, 1,2-propanediol, 1,2-dihydroxypropane, methylethylene glycol, propane-1,2-diol, E420 sorbitol, propylene glycol, polyethylene glycol (PEG) esters, PEG-20 stearate, PEG-40 stearate, PEG-150 stearate, PEG-150 distearate, PEG-100 stearate, laureth-12, ceteareth-20, laureth-23, glycereth-7, glycereth-12, glycereth-26, PEG-4, PEG-6, PEG-8, PEG-12, PEG-32, PEG-75, PEG-150, derivatives thereof, and mixtures thereof.

Chelating Agents

The presently preferred compositions may optionally further contain a chelating agent. Preferably, the presently preferred compositions comprise about 0.01% to about 1% by weight of a chelating agent. Preferred non-limiting examples of chelating agents include citric acid, isopropyl(mono) citrate, stearyl citrate, lecithin citrate, gluconic acid, tartaric acid, oxalic acid, phosphoric acid, sodium tetrapyrophosphate, potassium monophosphate, sodium hexametaphosphate, calcium hexametaphosphate, sorbitol, glycine (aminoacetic acid), methyl glucamine, triethanolamine (trolamine), EDTA, DEG (dihydroxyethylglycine), DPTA (diethylene triamine pentaacetic acid), NTA (Nitrilotriacetic Acid), HEDTA (N-(hydroxyethyl)-ethylenetriaminetriacetic acid), aminocarboxylates, dimercaperol (BAL), larixinic acid (Maltol), unidentate ligands (fluoride and cyanide ions), diphenylthiocarbazone, O-phenanthroline, barium diphenylamine sulfonate, sodium glucoheptonate, 8-hydroxyquinoline, olefin complexes (such as dicyclopentadienyl iron), porphyrins, phosponates, pharmaceutically acceptable salts thereof, derivatives thereof, and mixtures thereof.

In addition to those enumerated above, any other moisturizer, preservative, gelling agent, colorant or pigment, radical scavenger, surfactant, emulsifier, pH modifier, chelating agent, or other dermatologically acceptable excipient commonly known to those of ordinary skill in the art as useful in topical compositions is contemplated as useful in the methods described herein. Further, any non-toxic, inert, and effective topical carrier may be used to formulate the compositions described herein. Well-known carriers used to formulate other topical therapeutic compositions for administration to humans will be useful In these compositions. Examples of these components that are well known to those of skill in the art are described in *The Merck Index*, Thirteenth Edition, Budavari et al, Eds., Merck & Co., Inc., Rahway, N.J., (2001); the CTFA (Cosmetic, Toiletry, and Fragrance Association) *International Cosmetic Ingredient Dictionary and Handbook*, Tenth Edition (2004); and the "Inactive Ingredient Guide", U.S. Food and Drug Administration (FDA) Center for Drug Evaluation and Research (CDER) Office of Management, January 1996, the contents of which are hereby incorporated by reference in their entirety. Examples of such useful pharmaceutically acceptable excipients, carriers and diluents include distilled water, physiological saline, Ringer's solution, dextrose solution, Hank's solution, and DMSO, which are among those preferred for use herein.

These additional other inactive components, as well as effective formulations and administration procedures, are well known in the art and are described in standard textbooks, such as *Goodman and Gillman's: The Pharmacological Bases of Therapeutics*, 8th Ed., Gilman et al. Eds. Pergamon Press (1990) and *Remington's Pharmaceutical Sciences*, 17th Ed., Mack Publishing Co., Easton, Pa. (1990), both of which are incorporated by reference herein in their entirety.

In another particularly preferred embodiment, the presently preferred pharmaceutical compositions in the described methods are formulated in a lotion, cream, ointment, gel, suspension, emulsion, foam, aerosol, or other pharmaceutically acceptable topical dosage form.

Dosage

Appropriate dosage levels for the melatonin derivative agents contemplated in the preferred methods are well known to those of ordinary skill in the art and are selected to maximize the treatment of the previously described skin conditions.

If desired, other therapeutic agents can be employed in conjunction with those provided in the above-described methods. The amount of pharmaceutically active ingredients that may be combined with the carrier materials to produce a single dosage form will vary depending upon the host treated, the nature of the disease, disorder, or condition, and the nature of the active ingredients.

The preferred pharmaceutical methods may be single or multiple daily doses. In a preferred embodiment, the pharmaceutical compositions of the disclosed methods are given from one to three times daily. A preferred strategy is starting with a low dose twice daily and slowly working up to higher doses if needed.

It is understood, however, that a specific dose level for any particular patient will vary depending upon a variety of factors, including the activity of the specific skin protectant and/or emollient and pharmaceutically active agent; the age, body weight, general health, sex and diet of the patient; the time of administration; the rate of excretion; possible drug combinations; the severity of the particular condition being treated; and the form of administration. One of ordinary skill in the art would appreciate the variability of such factors and would be able to establish specific dose levels using no more than routine experimentation.

The optimal pharmaceutical formulations will be determined by one skilled in the art depending upon considerations such as the particular pharmaceutically active agent combination and the desired dosage. See, for example, "Remington's Pharmaceutical Sciences", 18th ed (1990, Mack Publishing Co., Easton, Pa. 10842), pp 1435-1712, the disclosure of which is hereby incorporated by reference. Such formulations may influence the physical state, stability, rate of in vivo release, and rate of in vivo clearance of the essential lipids.

In another preferred embodiment, the present preferred compositions may be used in combination with an additional pharmaceutical dosage form to enhance their effectiveness in treating any of the disorders described herein. In this regard, the present preferred compositions may be administered as part of a regimen additionally including any other pharmaceutical and/or pharmaceutical dosage form known in the art as effective for the treatment of any of these disorders.

Similarly, an additional topical pharmaceutically active agent, can be added to the present preferred compositions to enhance their effectiveness. Accordingly, this additional agent or additional pharmaceutical dosage form can be applied to a patient either directly or indirectly, and concomitantly or sequentially, with the preferred compositions described herein.

In one embodiment in this regard, the present preferred composition and the additional pharmaceutical dosage form can be administered to a patient at the same time. In an alternative embodiment, one of the present preferred compositions and the additional pharmaceutical dosage form can be administered in the morning and the other can be administered in the evening.

EXAMPLES

Overview of the Examples

A series of melatonin derivatives with anti-oxidant activity, as determined by a lipid peroxidation assay in brain extracts has been developed. The following examples show the methods and results of tests of melatonin and melatonin derivatives and their ability to protect against lipid peroxidation and ability to scavenge hydroxyl radicals. Melatonin and the melatonin derivatives showed significant activity in this area.

Synthesis of Melatonin Derivatives

The following examples illustrate the process by which the instant melatonin derivatives were synthesized. Moreover, the following examples are illustrative of preferred methods and are not intended to be limitations thereon. All percentages are based on the percent by weight of the final formulations prepared unless otherwise indicated and all totals equal 100% by weight.

Example 1

5-Methoxy-3-bis(nitromethyl)methylindole

A solution of 5-methoxyindole-3-carbaldehyde (7.96 g, 0.045 mol) and ammonium acetate (2.75 g, 0.035 mol) in nitromethane (50 $cm^3$) was refluxed under nitrogen for 7 hours using the method of John E. Macor et al. The mixture was concentrated under vacuum and partitioned between water and ethyl acetate, The organic layer was washed with brine, dried with Na$_2$SO$_4$, and evaporated under vacuum to produce 5-methoxy-3-bis(nitromethyl)methylindole.

Example 2

N-Acetylmelatonin, 2-Acetylmetlatonin, and 4-Acetylmelatonin

To a solution of melatonin (0.47 g, 2.02 mmol) in dichloromethane (15 cm$^3$) was added aluminium chloride (0.28 g, 2.05 mmol), followed by acetyl chloride (0.15 cm$^3$, 2.06 mmol) and the mixture was refluxed for 7 hours under nitrogen. HCl (20 cm$^3$, 0.1 M) was added to react with the excess aluminium chloride and the mixture was adjusted to pH 11 using 1 M aqueous NaOH, then extracted with dichloromethane. The organic layer was washed with saturated aqueous Sodium hydrocarbonate and saturated aqueous Sodium chloride, then dried over magnesium sulfate. After evaporation of the solvent, the residue was chromatographed on silica using petroleum ether and isopropanol (8:2, v/v) to produce 1-acetylmelatonin (0.12 g, 23%) as a brown solid. The second product 2-acetylmelatonin in the form of a white solid. The third product was 4-acetylmelatonin.

Example 3

1-Acetyl-4,5-dihydro-4-(5'-methoxyindol-3'-yl)-1H-pyrazole

To a stirred suspension of LiAlH$_4$ (1.83 g) in anhydrous THF (17 cm$^3$) under N$_2$ was added dropwise a mixture of 5-methoxy-3-(2'-nitroethenyl)indole and 5-methoxy-3-bis(nitromethyl)methylindole (1.76 g) in the THF (17 cm$^3$). Then the mixture was refluxed for 3 hours using the method of Spadoni et al. After cooling to 0° C., water was added dropwise to react with the excess hydride. The mixture was filtered through Celite and the filtrate concentrated under vacuum and partitioned between water and ethyl acetate. The organic layer was washed with brine, dried (MgS0$_4$) and concentrated under vacuum to give a crude solid. Without being purified, the mixture was dissolved in THF (25 cm$^3$) in a water-ice bath, to which TEA (2.8 cm$^3$) and acetic anhydride (1.8 cm$^3$) were added. The ice bath was removed and the solution was stirred for 15 hours using the method of Spadoni et al. The solvent was evaporated under vacuum and the residue was taken up in ethyl acetate and washed with a saturated aqueous solution of NaHCO$_3$, followed by saturated NaCl solution. The organic layer was dried with MgSO$_4$ and concentrated to give a crude solid, which was chromatographed on silica, using dichloromethane:methanol (98:2), to give 0.16 g of 1-acetyl-4,5-dihydro-4-(5'-dimethoxyindol-3'-yl)-1H-pyrazole as a brown oil.

Example 4

1-Acetyl-4,5-dihydro-4-(5',7'-dimethoxyindol-3'-yl)-1H-pyrazole

To a stirred suspension of LiAlH$_4$ (0.45 g, 12.2 mmol) in anhydrous THF (10 cm$^3$) under N$_2$ was added dropwise a solution of 5,7-dimethoxy-3-bis(nitromethyl)-methylindole (0.48 g, 1.7 mmol) in anhydrous THF, then the mixture was refluxed for 4 hours using the method of Spadoni et al. After cooling to 0° C., water was added dropwise to react with the excess hydride. The mixture was filtered through Celite and the filtrate concentrated under vacuum and partitioned between water and ethyl acetate. The organic layer was washed with brine, dried with MgSO$_4$ and concentrated under vacuum to give a crude solid. Without being purified, the mixture was dissolved in THF (14 cm$^3$) in a water-ice bath and TEA (1.2 cm$^3$) and acetic anhydride (0.74 cm$^3$) were added. The ice bath was removed and the solution stirred for 15 hours using the method of Gilberto Spadoni et al. The solvent was evaporated under vacuum, and the residue was take up in ethyl acetate and washed with a saturated aqueous solution of NaHC0$_3$, followed by saturated NaCl solution. The organic layer was dried with MgS0$_4$ and concentrated to give a crude solid, which was chromatographed on silica, using ethyl acetate:petrol (8:2), to give 60.8 mg (13%) of 1-acetyl-4,5-dihydro-4-(5',7'-dimethoxyindol-3'-yl)-1H-pyrazole as a brown oil.

Example 5

4,5-Dihydro-4-(5'-methoxyindol-3'-yl)-3H-pyrazole-N1-oxide

To a solution of sodium dithionite (85%, 16 g) in distilled water (68 cm$^3$), a solution of 5-methoxy-3-bis(nitromethyl)methylindole 17 (1.00 g, 3.6 mmol) in NaOH (2%, 54 cm$^3$), was added dropwise with stirring, using the method of Bezverkhii's. The mixture was heated at 70° C. for 4 hours. After the mixture was cooled and adjusted to pH 10, it was extracted with ethyl acetate. The ethyl acetate layer was dried with MgS0$_4$ and concentrated to collect a crude oil, which was chromatographed on silica, using petrol:ethyl acetate (4:6) to give 4,5-dihydro-4-(5'-methoxyindol-3'-yl)-3H-pyrazole-N1-oxide (0.17 g. 20%).

Example 6

4-Methoxymelatonin

To a cold solution of 4,5-dimethoxytryptamine (0.24 g, 1.1 mmol) in THF (10 cm$^3$), were added TEA (0.75 cm$^3$) and acetic anhydride (0.44 cm$^3$). The ice bath was removed and the solution was stirred for 7 hours using the method of Spadoni et al. The solvent was evaporated under vacuum and the residue was taken up into ethyl acetate and washed with a saturated aqueous solution of NaHC0$_3$, followed by saturated NaCL solution. The organic layer was dried with MgSO$_4$ and concentrated to give a crude solid, which was chromatographed on silica, using ethyl acetate:petrol (9:1), to give 0.24 g (48%) of 4-methoxymelatonin as a brown viscous oil.

Example 7

4,5-Dimethoxy-3-(2-nitroethenyl)-indole

A solution of 4,5-dimethoxyindole-3-carbaldehyde (0.21 g, 1.02 mmol) and ammonium acetate (0.1268 g, 1.60 mmol) in nitromethane (10 cm$^3$) was stirred at 70-75° C. under nitrogen for 11 hours using the method of Macor et al. The mixture was concentrated under vacuum and partitioned between water and ethyl acetate. The organic layer was washed with brine, dried with MgS0$_4$, and evaporated under vacuum to afford dimethoxy-3-(2-nitroethenyl)indole (0.25 g, 99%) as a brown solid.

Example 8

1-Acetyl-4,5-dihydro-4-(4',5'-dimetboxyindole-3'-yl)-1H-pyrazole

To a stirred suspension of LiAlH$_4$ (0.97 g, 21.1 mmol) in anhydrous THF (15 cm$^3$) under N$_2$ was added dropwise a mixture of 4,5-dimethoxy-3-(2'-nitroethenyl)indole and 4,5-dimethoxy-3-bis(nitromethyl)methylindole (1.1 g) in THF (15 cm$^3$), then the mixture was refluxed for 3 hours using the method of Gilberto Spadoni et al. After cooling to 0° C., water was added dropwise to react with the excess hydride. The mixture was filtered through Celite and the filtrate concentrated under vacuum and partitioned between water and ethyl acetate. The organic layer was washed with brine, dried with MgSO$_4$, and concentrated under vacuum to give a crude solid. Without being purified, the mixture was dissolved in the (15 cm$^3$) in a water-ice bath, then TEA (1.3 cm$^3$) and acetic anhydride (0.80 cm$^3$) were added. The ice bath was removed and the solution was stirred for 15 hours using the method of Spadoni et al. The solvent was evaporated under vacuum, and the residue was taken up in ethyl acetate and washed with a saturated aqueous solution of NaHCO$_3$, followed by saturated NaCl solution. The organic layer was dried with MgSO$_4$ and concentrated to give a crude solid, which was chromatographed on silica, using ethyl acetate:petrol (9:1), to give 0.13 g of 1-acetyl-4,5-dihydro-4-(4',5'-dimethoxyindole-3'-yl)-1H-pyrazole as a brown oil.

Example 9

4-[2'-(N-Acetyl)aminoethyl]-5,7-dimethoxyindole

To a cold solution of 4-(2'-aminoethyl)-5,7-dimethoxyindole (0.29 g, 1.3 mmol) in the (10 cm$^3$) were added TEA (0.9 cm$^3$) and acetic anhydride (0.5 cm$^3$). The ice bath was removed and the solution stirred for 15 hours using the method of Spadoni et al. The solvent was evaporated under vacuum, and the residue was taken up into ethyl acetate and washed with a saturated aqueous solution of NaHCO$_3$, followed by saturated NaCl solution. The organic layer was dried with MgSO$_4$ and concentrated to give a crude solid, which was chromatographed on silica, using ethyl acetate:methanol (95:5), to give 4-[2'-(N-acetyl)aminoethyl]-5,7-dimethoxyindole (0.19 g, 54%) as a brown viscous oil.

Example 10

5,7-Dimethoxy-3-bis(nitromethyl)methylindole

A solution of a mixture containing 5,7-dimethoxyindole-3-carbaldehyde and 4-carboxy-5,7-dimethoxyindole (2.93 g, 14 mmol) and ammonium acetate (0.89 g, 11.6 mmol) in nitromethane (40 cm$^3$) was heated at 80° C. under nitrogen for 7 hours. The mixture was concentrated under vacuum and partitioned between water and ethyl acetate. The organic layer was washed with aqueous saturated NaHCO$_3$ and brine, dried with MgSO$_4$, and evaporated under vacuum to collect a crude solid, which was chromatographed on silica, using petrol:ethyl acetate (7:3) to give 5,7-dimethoxy-3-bis(nitromethyl)methylindole as a brown solid.

Example 11

4,5-Dimethoxy-3-bis(nitromethyl)methylindole

A solution of 4,5-dimethoxyindole-3-carbaldehyde (0.10 g, 0.48 mmol) and sodium hydroxide (20 mg, 98%) in nitromethane (5 cm$^3$) was refluxed under nitrogen for 4 hours. The mixture was concentrated under vacuum and partitioned between water and ethyl acetate. The organic layer was washed with saturated aqueous NaHCO$_3$ and brine, dried with MgSO$_4$, and evaporated under vacuum to collect a crude solid, which was chromatographed on silica, using petrol:ethyl acetate (8:2), to give 4,5-dimethoxy3-bis(nitromethyl)methylindole as a pale yellow solid (77 mg, 51%).

Example 12

5,7-Dimethoxy-4-{2'-nitro-1'-(nitromethyl)ethyl}indole

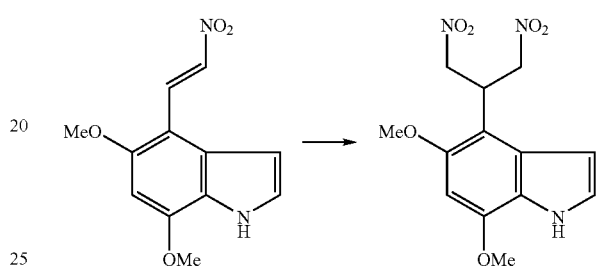

A solution of 5,7-dimethoxy-4-nitroethenylindole (0.82 g, 3.3 mmol) and NaHCO$_3$ (0.33 g) in nitromethane (15 cm$^3$) was refluxed under nitrogen for 30 hours. The mixture was then concentrated under reduced pressure and then partitioned between water (10 cm$^3$) and ethyl acetate (10 cm$^3$). The organic layer was washed with saturated aqueous NaHCO$_3$ (10 cm$^3$), then brine (10 cm$^3$), dried over MgSO$_4$ and evaporated under reduced pressure to give a crude solid, which was purified by chromatography on silica, eluting with petrol:ethyl acetate (80:20) to give 5,7-dimethoxy-4-{2'-nitro-1'-(nitromethyl)ethyl}indole as a pale yellow solid (0.64 g, 63%)

Example 13

1-Acetyl-4,5-dihydro-4-(5',7'-dimethoxyindol-4'-yl)-1H-pyrazole

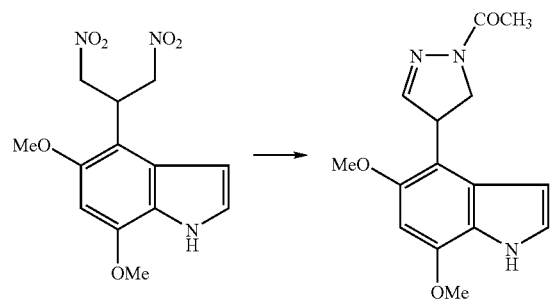

To a stirred suspension of LiAlH$_4$ (0.44 g, 11.6 mmol) in anhydrous THF (15 cm$^3$) under nitrogen was added dropwise a mixture of 5,7-dimethoxy-4-{2'-nitro-1'-(nitromethyl)ethyl}indole (0.6 g, 1.9 mmol) in THF (15 cm$^3$), then the solution was refluxed for 1 hours according to the method of Spadoni et al. After cooling to 0° C., water was added dropwise to decompose the excess hydride, the mixture was filtered through celite and the filtrate concentrated under reduced pressure, then partitioned between water (10 cm$^3$) and ethyl acetate (10 cm$^3$). The organic layer was washed with brine (10 cm$^3$), dried over MgSO$_4$ and concentrated under reduced pressure to give a crude solid. This crude solid was dissolved in THF (10 cm$^3$) in an ice-water bath then triethylamine (1.2 cm$^3$) and acetic anhydride (0.73 cm$^3$) were added. The ice bath was removed and the solution was stirred for 15 hours. The solvent was evaporated under vacuum and the residue was dissolved in ethyl acetate (15 cm$^3$), washed with a saturated aqueous solution of NaHCO$_3$ (15 cm$^3$), followed by saturated NaCl solution (15 cm$^3$). The organic layer was dried over MgSO$_4$ and concentrated to give a crude solid, which was purified by chromatography on silica, eluting with ethyl acetate:petrol (60:40) to give 1-acetyl-4,5-dihydro-4-(5',7'-dimethoxyindol-4'-yl)-1H-pyrazole (0.086 g, 16%).

Example 14

Antioxidant Test

TBA Assay

Reagents, Chemicals and Equipment

Ascorbic acid and propylgallate were purchased from Aldrich. N-Butanol and ethanol were purchased from BDH. Butylated hydroxytoluene (BHT), bovine brain extract, FeCl$_3$, thiobarbituric acid (TBA) and PBS (phosphate buffered saline) tablets were purchased from Sigma. For spectroscopic measurements, a UNICAM UVNIS Spectrometer (UV2) was used. A well-controlled water bath was utilized for incubating the test system at the required temperatures. Plastic falcon tubes were used to accommodate the assay. Accurate pipettes were used to dispense the reagents.

Preparation of Liposomes and Reagents

The following liposomes and reagents were prepared in order to carry out the experiments.

1. Brain extract (50 mg) was weighed into a clean universal container. About 7 glass balls and 10 cm$^3$ of PBS were added. The mixture was sonicated in an ice-water bath until the lipid was suspended and the suspension was homogeneous and milky in appearance. The suspension was kept cool during the sonication, although care was taken not to overfill the bath with ice as the sonication becomes relatively ineffective.
2. Ascorbic acid (0.0176 g) was dissolved in deionised water and diluted in 100 cm$^3$ of volumetric flask.
3. Ferric chloride hexahydrate (0.0270 g) was dissolved in deionized water and diluted in 100 cm$^3$ of volumetric flask.
4. Sodium hydroxide (1 g) was dissolved in 500 cm$^3$ of deionized water.
5. Phosphate buffered saline was prepared (PBS, pH=7.4).
6. HCl (338 cm$^3$, 37%) was diluted with 162 cm$^3$ deionized water to give 500 cm$^3$ of 25% HCl.
7. BHT (5 g) was dissolved in 250 cm$^3$ ethanol.
8. TBA (5 g) was added to 500 cm$^3$, 50 mM NaOH, and the solution was heated with stirring to dissolve all the TBA.
9. PG (0.1061 g) was dissolved in 500 cm$^3$ deionized water.
10. A stock solution of test compound at 10 mg/cm$^3$ was prepared, the concentration depended on the estimated activity of the substance, and serial dilutions were made to obtain 5.0, 2.5, 1.25, 0.625, 0.3125 and 0.15625 mg/cm$^3$. The stock solution and these six dilutions were screened in the lipid peroxidation—TEA test, in attempt to obtain a dose response curve for antioxidant efficacy against concentration for the substance.

Procedure

Sixty-eight centrifuge tubes were numbered.

1. Test substance (0.1 cm$^3$) was added to tubes; 10 mg/cm$^3$ to No. 13-20 of tubes, 5 mg/cm$^3$ to No. 21-28, 2.5 mg/cm$^3$ to No. 29-36, 1.25 mg/cm$^3$ to No. 37-44, 0.625 mg/cm$^3$ to No. 45-52, 0.3125 mg/cm$^3$ to No. 53-60, 0.15625 mg/cm$^3$ to No. 61-68.
2. PG (0.1 cm$^3$) was added to 9-12.
3. Ethanol (0.1 cm$^3$) was added to No. 5-8.
4. Deionized water (0.3 cm$^3$) was added to No. 1-4, deionized water (0.4 cm$^3$) was added to No. 17-20, 25-28, 33-36, 41-44, 49-52, 57-60, and 65-68.
5. Liposome (0.2 cm$^3$) was added to No. 1-4, 5-8, 9-12, 13-16, 21-24, 29-32, 37-40, 45-48, 53-56 and 61-64.
6. PBS (0.5 cm$^3$) was added to all tubes.
7. Ferric chloride (0.1 cm$^3$, 1 mM) was added to No. 5-8, 9-12, 13-16, 21-24, 29-32, 37-40, 45-48, 53-56, and 61-64.
8. Ascorbic acid (0.1 cm$^3$, 1 mM) was added to No. 5-8, 9-12, 13-16, 21-24, 29-32, 37-40, 45-48, 53-56 and 61-64.
9. The tubes were incubated at 37° C. for 30 min.
10. BHT (0.1 cm$^3$, 2%), TBA (0.5 cm$^3$, 1%) and HCl (0.5 cm$^3$, 25%) were added to all tubes.
11. The tubes were heated at 85-90° C. for 30 mM.
12. The tubes were removed from heater and cooled.
13. N-Butanol (2.5 cm$^3$) was added to all tubes. The tubes were then shaken to mix and spun at 3500 rpm at room temperature for 10 min.
14. N-Butanol (2.5 cm$^3$) was removed and placed in cuvettes.
15. Absorbance at 532 nm on a spectrophotometer was recorded, using n-butanol as blank.
16. The mean and standard deviation were calculated. The % inhibition was calculated using equation (1).

$$\% \text{ Inhibition} = 100 \times \frac{(FRM-B) - (ST-B-SA)}{(FRM-B)} \quad \text{Eqn (1)}$$

All data are expressed and mean±SEM (n=4). % inhibition was used to construct the graph and calculate IC$_{50}$.

Example 15

Cell Line Test (MTT)

Reagents, Chemicals and Equipment

3-[4',5'-Dimethylthiazol-2'-yl]-2,5-diphenyltetrazolium bromide (MTT), dimethyl sulphoxide (DMSO), isopropranol, foetal calf serum, and trypan blue were purchased from Sigma-Aldrich. Trypsin 250 was purchased from DIFCO. Ethylenediaminetetraacetic acid (EDTA), glucose, sodium phenol red, sodium chloride, potassium chloride, sodium hydrogen carbonate, potassium dihydrogen phosphate, and disodium hydrogen phosphate were purchased from BDH. Keratinocyte-SFM was purchased from GIBCO. For spectroscopic measurements, MRX Microplate Reader was used, which was controlled by Revelation Version 3.04.

Preparation of Solutions

The following solutions were prepared for use in the cell line test (MTT).

1. Sodium chloride (8 g), potassium chloride (0.2 g), disodium hydrogen phosphate (1.15 g) and potassium dihydrogen phosphate (0.2 g) were dissolved in deionized water (1 L). This PBS solution was warmed to 37° C. at the time of use.
2. Trypsin 250 (2.5 g), EDTA (0.2 g), glucose (1.0 g), potassium chloride (0.4 g), sodium chloride (8.0 g), sodium phenol red (0.002 g), and sodium hydrogen carbonate (0.58 g) were dissolved in deionized water (1 L). This solution was warmed to 37° C. at the time of use.
3. Trypsin inhibitor solution was created by using feotal calf (1 ml) and was diluted in 100 ml of PBS.
4. MTT powder (0.125 g) was dissolved in PBS buffer (25 ml) to give 5 mg/ml of MTT stock solution, which was stored at −20° C. and wrapped in foil to protect from light to create MTT stock solution.
5. MTT stock solution was defrosted and diluted 1 in 10 in PBS buffer to give 0.5 mg/ml of working solution, which was prepared at the time of use to create an MTT working solution.
5. Trypan blue solution was created by dissolving Trypan blue (0.04 g) in deionized water (10 ml).

Preparation of Test Cells

The cell culture consisted of an HPV-16 immortalized human keratinocyte cell line from American Type Culture Collection (ATCC).

Cells were cultured in Serum-Free Keratinocyte Medium (Keratinocyte-SFM) supplemented with recombinant epidermal growth factor (rEGF) and bovine pituitary extract (BPE) in a T-75 flask under conditions of 5% $CO_2$ at 37° C. Fluid in the flask was changed with fresh complete medium every 3 days.

When cells grew to 60-80% confluence as determined under a microscope, the flask was washed with PBS. Small amount of trypsin-EDTA solution (1-2 ml) was added to the flask and incubated for 5 minutes at 37° C. When approximately 90% of the cells were dislodged, trypsin inhibitor solution (10 ml) was added to stop trypsin reaction. The cells were spun at 500 rpm for 10 minutes at room temperature. The cell pellet was gently resuspended in 10 ml of media. The basal cells were counted with a haemocytometer by adding trypan blue solution to determine viable cells. The cells were adjusted the density to $1 \times 10^5$ cells/mL in media.

Preparation of Test Compound Solutions

A stock solution of each compound was prepared by dissolving compound (20 mg) in DMSO (1 ml), to give 20 mg/mL of stock solution.

A working solution was prepared by diluting a stock solution (20 μl) into media (1.98 ml) to give 200 μg/mL of working solution.

Procedure

The following steps were performed to carry out the MMT experiment. 100 μl of resuspended cell suspension was added to test wells in 96-well plate, omitting column 11. Media was aspirated from each well after plate was incubated for 24 hours at 37° C., 5% $CO_2$, then wells were washed with PBS. 100 μl of media containing 1% DMSO was added to each test well, omitting column 2. 200 μl of working solution of compound was added to each the wells, B2 to G2. 100 μl of solution was transferred to perform serial dilutions across the plate from column 2 up to column 9, and 100 μl of solution was discard from column 9. The plate was incubated for 3 days at 37° C., 5% $CO_2$. Media was removed, and wells were washed with PBS. Then 200 μl of MTT working solution was added to each well. After the plate was incubated for 2 hours at 37° C., MTT solution was removed and wells were washed with PBS. 200 μl of DMSO-isopropanol solution (1:9) was added to each well, and the plate was left at room temperature for 10 minutes wrapped in foil. The plate was read using MRX Microplate Reader at 595 nm and 630 nm as reference.

Results of TBA and MTT Assays

Based on the TBA and MTT assays, the tested compounds were classified into different groups by their activities (See Table 1).

Melatonin, Alva, N-acetylserotonin and serotonin were inactive against human papilloma virus-16 (HPV-16) immortalized keratinocyte proliferation, but they showed significant activity in scavenging hydroxyl radicals with $IC_{50}$ values below 1 mM. A number of studies strongly suggested that melatonin was also a scavenger of nitric oxide, which implicated melatonin and its analogues as potential anti-inflammatory agents. Any anti-psoriatic activity in these compounds is likely to lie with the antioxidant ability.

4,5-Dimethoxy-3-[bis(2-nitromethyl)methyl]indole; 5-methoxy-3-(2'-nitroethenyl)indole; and 5,7-dimethoxy-3-bis(nitromethyl)methylindole These three compounds showed an anti-proliferative effect, especially, 5-methoxy-3-(2'-nitroethenyl)indole and 5,7-dimethoxy-3-bis(nitromethyl)methylindole. However, compared with the melatonin group, these compounds showed less ability to scavenge hydroxyl radicals and protect against lipid peroxidation.

5,7-Dimethoxy-4-(2'-nitroethenyl)indole; 5,7-dimethoxy-3-(2'-nitroethenyl)indole; 4,5-dimethoxy-3-(2'-nitroethenyl)indole; and 5-methoxytryptamine These compounds showed good activity as antioxidants and anti-proliferative agents; in particular, 5,7-dimethoxy-4-(2'-nitroethenyl)indole, 5,7-Dimethoxy-3-(2'-nitroethenyl)indole, 4,5-dimethoxy-4-(2'-nitroethenyl)indol had very low $IG_{50}$ values comparative to dithranol. However, these compounds appeared to induce apoptosis in the keratinocyte cell line and may exhibit greater toxicity.

4-(2'-Aminoethyl)-5,7-dimethoxyindole; 4,5-dimethoxytryptamine; 4-methoxymelatonin; 1-acetyl-4,5-dihydro-4-(5'-dimethoxyindole-3-yl}-1H-pyrazole; and N-ethylformylmelatonin These five compounds had their $IG_{50}$ values below 200 μM and $IC_{50}$ values below 0.30 mM (Table 1), in particular, 4-(2'-aminoethyl}-5,7-dimethoxyindole and 4,5-dimethoxytryptamine were significantly active in both anti-proliferation and antioxidant tests with the $IG_{50}$ value below 100 μM and $IC_{50}$ value below 0.10 mM. 4-Methoxymelatonin, 1-acetyl-4,5-dihydro-4-(5'-dimethoxyindole-3'-yl)-1H-pyrazole and N-ethylformylmelatonin, which are derivatives of melatonin, showed almost the same antioxidant activity as melatonin, but much more activity than melatonin as antiproliferative agents. The results support further consideration of these compounds as potential anti-psoriatic agents because they showed not only antioxidant activity, but also anti-proliferative activity.

Table 1 shows the results of the MTT and TBA assays for the aforementioned compounds.

TABLE 1

| Compound | MTT assay IG$_{50}$ (µM) | TBA assay IC$_{50}$ (mM) |
|---|---|---|
| Melatonin | >862.07 | 0.14 |
| AMK | 407.8 | 0.28 |
| N-Acetylseratonin | >917.43 | 0.75 |
| 5-Methoxy-3-(2-nitroethenyl)-indole | 15.54 | 2.51 |
| 5,7-Dimethoxy-3-bis(2-nitromethyl)methyl-indole | 20.24 | 1.66 |
| 4,5-Dimethoxy-3-bis(2-nitromethyl)methyl-indole | 126.10 | 1.91 |
| 5,7-Dimethoxy-4-(2-nitroethenyl)-indole | 6.62 | 0.60 |
| 5,7-Dimethoxy-3-(2-nitroethenyl)-indole | 13.54 | 0.81 |
| 4,5-Dimethoxy-3-(2-nitroethenyl)-indole | 22.04 | 0.44 |
| 4-(2-Aminoethyl)-5,7-dimethoxyindole | 53.90 | 0.051 |
| 4,5-Dimethoxytryptamine | 82.53 | 0.097 |
| 4-Methoxymelatonin | 118.70 | 0.28 |
| 1-Acetyl-4,5-dihydro-4-(5'methoxyindol-3'-yl)-1H-pyrazole | 150.30 | 0.21 |
| 5,7-Dimethoxy-4-bis(nitromethyl)methylindole | 145 | 3.97 |
| 1-Acetyl-4,5-dihydro-4-(5',7'-dimethoxyindole-4'yl)-1H-pyrazole | 355 | 1.79 |

Accordingly, it would further be expected that the methods of administering the present melatonin derivative compositions are more effective in reducing or treating symptoms associated with oxidative damage to a patient than methods which do not include a melatonin derivative as an active agent.

Additionally, it would be expected that the results herein described would be similarly observed for any period of treatment or treatment regimen useful for treating patients with symptoms associated with oxidative damage or for preventing oxidative damage to a patient. This includes daily administration of the melatonin derivatives and pharmaceutically acceptable carriers topically during the period of treatment, one or more daily administration of the topical compositions, or intermittent administration of the topical compositions. Further, the period of treatment contemplated herein can be any sufficient period of time to observe the desired physiological effect, for example from about 2 minutes to about 4 hours, but in most cases more than 30 minutes, minimum.

Intermittent administration contemplated herein includes administration conducted other than daily administration. Such intermittent administration is typically conducted when a patient commences a new treatment, as a treatment is in its final stages (i.e. as the patient is weaned off of the treatment), or as part of a maintenance regimen. Typically, intermittent administration is conducted more than once per week, but less than once per day. This intermittent treatment is especially useful when a patient starts a new treatment regimen to build their tolerance to the new medicine, and is typically followed by a more regular administration regimen.

Accordingly, further contemplated herein is the intermittent administration of the topical composition after said period has ended to maintain the reduced the harmful effects ameliorated with the methods herein described.

The present subject matter being thus described, it will be apparent that the same may be modified or varied in many ways. Such modifications and variations are not to be regarded as a departure from the spirit and scope of the present subject matter, and all such modifications and variations are intended to be included within the scope of the following claims.

We claim:
1. A compound having the formula:

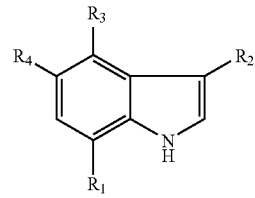

wherein:
R$_1$ is hydrogen, C$_1$-C$_6$ alkyl, C$_2$-C$_6$ alkenyl, C$_1$-C$_6$ alkoxy, or C$_2$-C$_6$ alkenoxy;
R$_2$ is C$_1$-C$_6$ alkyl-NHCOCH$_3$ or C$_2$-C$_6$ alkenyl-NHCOCH$_3$;
R$_3$ is CO(C$_1$-C$_6$ alkyl), CO(C$_2$-C$_6$ alkenyl), C$_1$-C$_6$ alkoxy, or C$_2$-C$_6$ alkenoxy; and
R$_4$ is C$_1$-C$_6$ alkoxy or C$_2$-C$_6$ alkenoxy.

2. The compound of claim 1, wherein
R$_1$ is hydrogen,
R$_2$ is CH$_2$CH$_2$NHCOCH$_3$,
R$_3$ is COCH$_3$, and
R$_4$ is OCH$_3$.

3. The compound of claim 1, wherein
R$_1$ is hydrogen,
R$_2$ is CH$_2$CH$_2$NHCOCH$_3$,
R$_3$ is OCH$_3$, and
R$_4$ is OCH$_3$.

4. The compound of claim 1, wherein said compound is selected from the group consisting of:
4-Acetylmelatonin;
4-Methoxymelatonin;
and
a pharmaceutically acceptable salt or derivative thereof.

5. A nutritional, pharmaceutical or cosmetic composition comprising the compound of claim 1 and a pharmaceutically acceptable carrier.

6. The compound of claim 1, wherein the compound is an antioxidant.

7. A method of protecting a mammal against the effects of free radicals comprising administering to a mammal in need thereof an amount of the compound of claim 1 which is effective to protect against the effect of said free radicals.

8. A method of inhibiting or treating free radical induced disease states selected from the group consisting of emphysema, viral hepatitis, tuberculosis, psoriasis, atherosclerosis, systemic lupus erythematosus, cancer and heightened LDL cholesterol by administering the compound of claim 1.

9. A method of prolonging the shelf life of cosmetic and personal care items that are susceptible to rancidity, wherein the compound of claim 1 is mixed with a cosmetic or personal care item.

10. A method of treating a patient afflicted with a chronic inflammatory disease comprising administering to the patient a therapeutically effective amount of the compound of claim 1.

11. The method of claim 7 wherein the compound is selected from the group consisting of 4-Acetylmelatonin; 4 Methoxymelatonin; and pharmaceutically acceptable salts or derivatives thereof.

12. The method of claim 8 wherein the compound is selected from the group consisting of 4-Acetylmelatonin; 4-Methoxymelatonin; and pharmaceutically acceptable salts or derivatives thereof.

13. The method of claim 9 wherein the compound is selected from the group consisting of 4-Acetylmelatonin; 4-Methoxymelatonin; and pharmaceutically acceptable salts or derivatives thereof.

14. The method of claim 10 wherein the compound is selected from the group consisting of 4-Acetylmelatonin; 4-Methoxymelatonin; and pharmaceutically acceptable salts or derivatives thereof.

* * * * *